United States Patent [19]

Burbank, III et al.

[11] Patent Number: 4,787,387
[45] Date of Patent: Nov. 29, 1988

[54] SURGICAL CLOSURE ELEMENT

[75] Inventors: John E. Burbank, III, Ridgefield; John R. Montgomery, Fairfield, both of Conn.

[73] Assignee: American Cyanamid Company, Stamford, Conn.

[21] Appl. No.: 24,929

[22] Filed: Mar. 13, 1987

Related U.S. Application Data

[63] Continuation of Ser. No. 669,497, Nov. 8, 1984, abandoned.

[51] Int. Cl.$^4$ ................ A61B 17/04; F16B 35/04
[52] U.S. Cl. ............................. 128/334 R; 411/457
[58] Field of Search ............... 128/335; 411/457; 227/19

[56] References Cited

U.S. PATENT DOCUMENTS

| | | | |
|---|---|---|---|
| 2,910,067 | 10/1959 | White | 128/334 |
| 3,753,438 | 8/1973 | Wood et al. | 128/335 |
| 4,014,492 | 3/1977 | Rothfuss | 227/19 |
| 4,043,504 | 8/1977 | Hueil et al. | 227/116 |
| 4,321,002 | 3/1982 | Froehlich | 411/457 |
| 4,465,071 | 8/1984 | Samuels et al. | 128/335 |
| 4,523,707 | 6/1985 | Blake, III et al. | 227/19 |

FOREIGN PATENT DOCUMENTS

| | | | |
|---|---|---|---|
| 273146 | 4/1951 | France | 411/472 |
| 529968 | 7/1955 | Italy | 411/457 |

Primary Examiner—Richard C. Pinkham
Assistant Examiner—Gary Jackson
Attorney, Agent, or Firm—David A. Warmbold; Charles F. Costello

[57] ABSTRACT

An improved surgical instrument cartridge is described. The cartridge comprises a plurality of wound closure elements. Each element has a crown and two opposite side legs. The distal end of each leg of an element contacts the crown of the adjacent preceding element. Two opposite grooves (in the cartridge) contain at least each end of each crown and the proximal end of each leg. The cartridge is attached to a surgical instrument. To activate the plurality of closure elements, a spring acts only on the proximal element. The improvement comprises the distal ends of the legs of each element being in an essentially converging relationship. The plurality of elements are thus self-aligning in the grooves. The wound closure element can be a staple.

4 Claims, 2 Drawing Sheets

SURGICAL CLOSURE ELEMENT

This application is a continuation of application Ser. No. 669,497, filed Nov. 8, 1984, abandoned May 22, 1987.

BACKGROUND OF THE INVENTION

This invention relates to an improved surgical wound closure element. The improvement allows for the sequential motion without jamming, of a plurality of closure elements in a feed track. In the feed track, the legs of an element are adjacent the crown of a preceding element. This invention specifically relates to a feed track containing two or more surgical wound closure elements. The invention can be useful in a ligating instrument containing a plurality of ligating clips and is useful in a surgical stapler containing a plurality of staples. See, e.g., an improved surgical stapler described in U.S. Pat. Nos. 4,618,086 issued Oct. 21, 1986 or 4,634,035 issued Jan. 6, 1987. These patents are incorporated by reference.

This invention decreases the frictional resistance between the plurality of closure elements and the feed track. An advantage of this is that the force required to linearly move a plurality of closure elements in the feed track is reduced. Another advantage is that a greater number of closure elements can be loaded into a surgical cartridge or magazine.

In combination with either or both U.S. Pat. Nos. 4,618,086 and 4,634,035, which are incorporated by reference, the improvement to the closure element cartridge enables the use of a very thin feed delivery system. This advantage cannot be overemphasized. Specifically, this advantage provides greater visibility of the crimping mechanism, e.g. an anvil for a surgical staple or a pair of jaws for a ligating clip, and therefore vastly improves, if not insures, proper placement of a closure element at the wound site.

This invention makes possible the feeding of a plurality of closure elements in a surgical instrument cartridge, e.g. a plurality of more than about twenty, which are sequentially in direct contact with one another in a leg to crown configuration.

It is an object of this invention to minimize friction in a feed track. The friction magnifies exponentially with the number of closure elements in the feed track.

SUMMARY OF THE INVENTION

A surgical instrument cartridge is described. The cartridge comprises a plurality of wound closure elements. Each element has a crown and two opposite side legs. The distal end of each leg of a wound closure element contacts the crown of the adjacent preceding element.

The instrument cartridge also comprises means for containing at least each end of each crown and the proximal end of each leg in the cartridge. Further, the cartridge comprises means for attaching the cartridge to a surgical instrument.

The invention comprises an improvement to the surgical instrument cartridge. The improvement comprises the distal ends of the legs of each element being in an essentially converging relationship. Alternatively, the improvement comprises a deformation adjacent each end of each crown. The distal end of each leg of an element contacts the respective deformation of the adjacent preceding element. The utility of the improvement is that a plurality of elements are self-aligning in the cartridge containing means.

In one embodiment, each element is a staple. In another embodiment each element is a clip. In yet another embodiment, the cartridge containing means are two opposite grooves. The two opposite grooves can be singularly described as a feed track.

In the alternative improvement comprising a deformation adjacent each end of each crown, a further improvement comprises the distal ends of the legs of each element being in an essentially converging relationship.

DESCRIPTION OF THE INVENTION

A column of two or more wound closure elements being sequentially moved in a leg to crown fashion can employ this invention. The amount of convergence in the legs either independent of or combined with the amount of bend in the crown, can vary.

A bend in the closure element crown is not necessary, see for example FIGS. 1, 2, 9, 10 and 14, if the closure element legs can be otherwise deflected inward so they do not ride onto the arc between each end of the crown and each leg.

Side thrust is a component of forward thrust. It is created when one of the distal ends of a leg moves laterally. For a particular closure element, the side thrust is in direct proportion to the forward thrust. Side thurst can be calculated as a function of the imbalance between the two instantaneous slopes experienced by the distal ends of each leg (the slopes are relative to a plane which is perpendicular to the direction of the desired forward motion).

Side thrust by a closure element causes resistance to the forward motion of the column of closure elements. This is due to the friction between the closure element and the walls of the cartridge (or magazine) tracks. The amount of friction is the product of the side thrust multiplied by the coefficient of friction between the closure element and the tracks.

The force required to move the column of closure elements, as seen by any particular closure element, is increasing by the side thrust multiplied by the coefficient of friction. Since the side thrust is in direct proportion to the forward thrust, each closure element closer to the force necessary to move the column of closure elements, is resisting forward motion more than the preceding closure element. This is due to the increased forward thrust received. The total frictional loss of the column of closure elements in the cartridge tracks is the sum of the frictional losses of each closure element. When the total frictional loss is greater than or equal to the force necessary to move the column of closure elements, the most distal closure element cannot move.

Due to the above described exponential reaction possible with a plurality of closure elements, it is desirable to relieve the source of side thrust. One way to do this is to use closure elements whose ends are convrging toward each other sufficiently so that they contact only a flat area or balanced slopes on the preceding closure element crown. Providing a bend to the preceding crown is one way of doing this. Providing a deformation adjacent each end of each closure element crown, such as notches, dents, steps or similar means for guiding is also a way. Relieving the source of side thurst allows more closure elements to be contained in a cartridge.

The term wound closure element is intended to be generic and includes, but is not limited to, a staple, clip, clamp, fastener, pin, or a similar closure element. A surgical staple is preferred. The wound closure element exemplified in FIGS. 1 to 14 is a surgical staple.

Figures 9, 10:
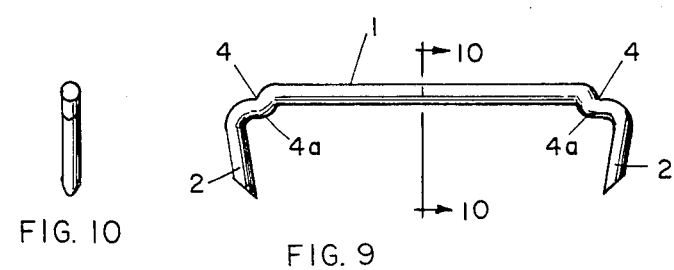
FIG. 9 is a front view showing a deformation adjacent each end of the crown of a wound closure element.
FIG. 10 is a cutaway side view taken on the plane 10—10 of FIG. 9.

Referring to FIGS. 1 to 10, a surgical wound closure element has a crown 1. Two opposite side legs 2 are contained at each opposite end of the crown 1. The improvement of this invention comprises the distal ends of the opposite side legs 2 of each element being in an essentially converging relationship (FIGS. 1 and 2); at least one bend 3 in the crown (FIGS. 3 to 8 and 11 to 13); and a deformation 4 adjacent each end of each crown 1, the distal end of each leg 2 of an element contacting the respective deformation of the preceding element (FIGS. 9, 10 and 14).

The direction of the bend 3 can be in the direction of each side leg 2. The bend enables at least the distal ends of the legs 2 of each element to be in an essentially converging relationship.

Referring to FIGS. 3 to 6, 11 and 12, two bends 3 are essentially equidistant from the center of the crown 1.

Figures 1, 2:
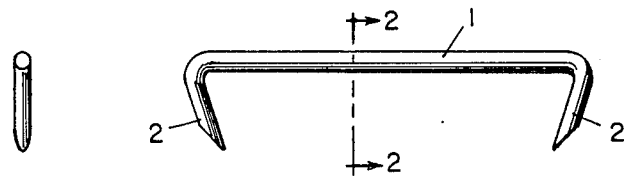
FIG. 1 is a front view showing the legs of a wound closure element in a converging relationship.
FIG. 2 is a cutaway side view taken on the plane 2—2 of FIG. 1.
Figures 3, 4:
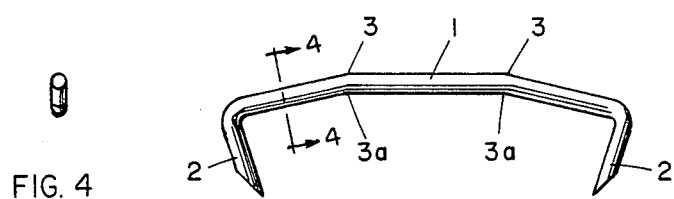
FIGS. 3, 5 and 7 are front views showing at least one bend in each crown of a wound closure element and the legs of each element in a converging relationship.
FIGS. 4, 6 and 8 are cutaway side views taken on the plane 4—4 of FIG. 3, the plane 6—6 of FIG. 5, and the plane 8—8 of FIG. 7, respectively.
Figures 5, 6:
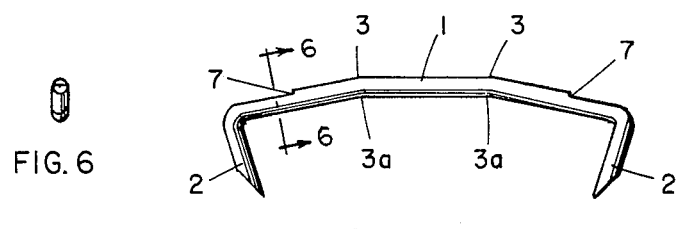
Figures 7, 8:
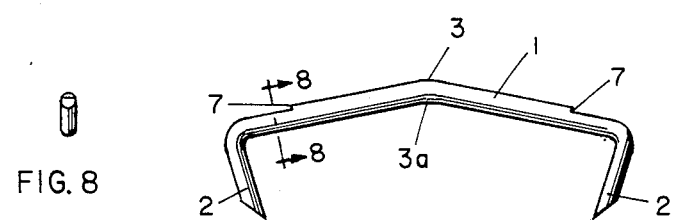
Figure 12:
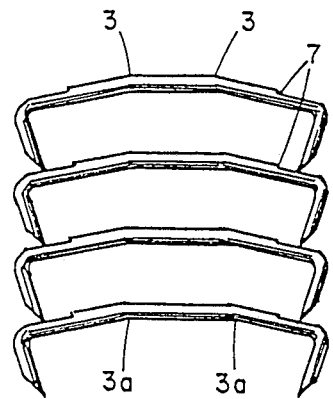
FIGS. 12 to 14 are alternative embodiments to the plurality of wound closure elements shown in FIG. 11.
Figure 13:
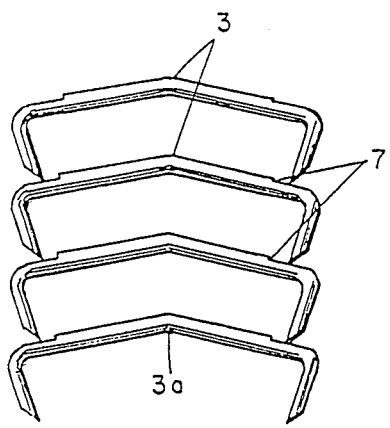
Figure 14:
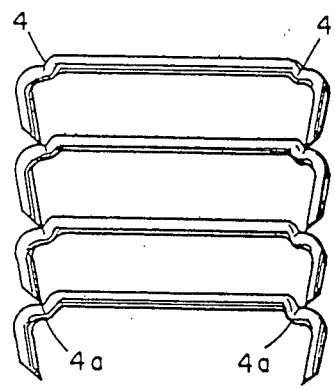

Referring to FIGS. 7, 8 and 13, the bend 3 is essentially at about the center of the crown 1. Referring to FIGS. 5 to 8, 12 and 13, the notches 7 are about equidistance from the center of the crown 1. The notches, which are optional, can be used as a stop by the distal ends (which can be pointed) of an adjacent wound closure element.

Referring to FIGS. 3, 5, 7 and 11 to 13, the bend 3a on the underside of the crown 1 can be formed during the manufacture of the bend 3. It is to be understood that the bend 3a is not critical to the practice of this invention. That is, alternative wound closure elements may be manufactured having an essentially triangular shaped crown, wherein the lower portion of the crown is essentially planar.

Referring to FIGS. 9, 10 and 14, an alternative wound closure element is described. The wound closure element has a crown 1 and two opposite side legs 2. The improvement comprises a deformation 4 at about each end of the crown 1. At least the distal ends of each leg 2 can also be in an essentially converging relationship.

Referring to FIGS. 11 to 14, a surgical cartridge 5 is disclosed. The cartridge comprises a plurality of wound closure elements. The elements shown in FIGS. 11 to 14 are essentially a plurality of the elements shown in FIGS. 3, 5, 7 and 9, respectively.

Each wound closure element comprises a crown 1 and two opposite side legs 2. The relationship of each wound closure element to the adjacent element in the cartridge is a point to crown relationship. That is, at least the distal ends of the legs (which can be pointed) of a wound closure element contact the crown 1 of the preceding element. But for the point to crown relationship, each wound closure element is in an essentially noncontiguous relationship to the adjacent element.

Referring again to FIG. 11, besides a plurality of wound closure elements, the surgical cartridge 5 comprises a means 6 for containing at least the ends 1a of each crown and the proximal ends 2a of each leg. Preferably, the contacting means are two opposite grooves. Although not shown, the cartridge 5 can also contain means for attaching the cartridge to a surgical instrument, and means for biasing the plurality of closure elements along the staple track towards the anvil. The attaching and the biasing means are known in the prior art. Please see, for example, U.S. Pat. Nos. 4,196,836 issued Apr. 18, 1980 and 4,043,504 issued Aug. 23, 1977, and 4,618,086. The patents are incorporated herein by reference. The improvement to the cartridge of this invention allows the plurality of elements to be self-aligning in the containing means 6.

Figure 11:
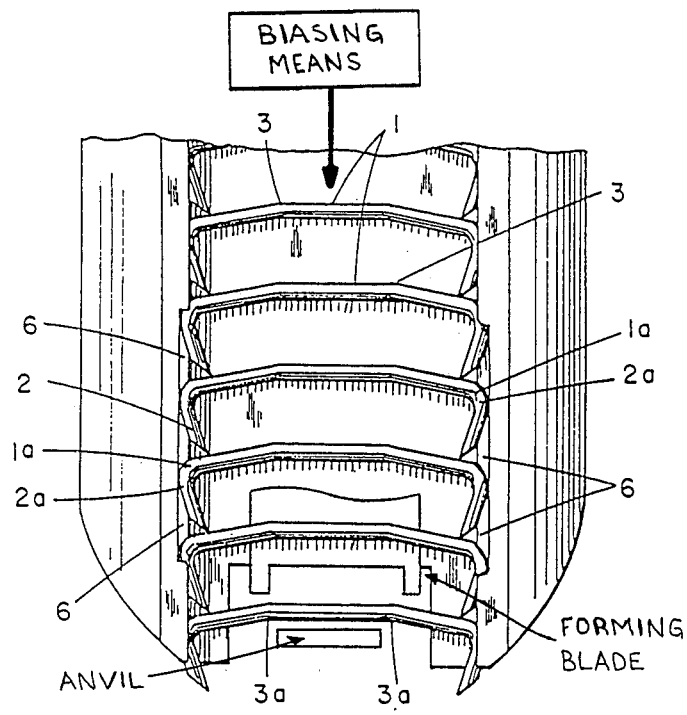
FIG. 11 is a cutaway front view of a surgical instrument cartridge showing a plurality of wound closure elements, the distal end of each leg of a wound closure element contacting the crown of the adjacent preceding element.

It is to be understood that the plurality of wound closure elements described in FIGS. 12 to 14 can be alternatively used in the cartridge 5 shown in FIG. 11. That is, it is to be understood that the wound closure elements shown in FIGS. 12 to 14 are interchangeable with the wound closure elements shown in FIG. 11.

In a final embodiment, the distal ends of the grooves 6 are adjacent to an anvil. A description of an anvil which can be used to practice this embodiment is disclosed in the prior art, for example the U.S. patents described above, or U.S. Pat. No. 4,634,045 which is incorporated herein by reference.

We claim:

1. An improved surgical stapler of the type having a cartridge and a handle, the cartridge, having means for forming a staple including an anvil and a forming blade, and a staple feed track movably containing a plurality of surgical staples and means for biasing the staples toward the anvil, each staple having a crown, and two opposite side legs; and the handle having means for activating said forming means, the activating means in said handle being cooperatively attached to said forming means in said cartridge, the improvement comprising in combination the distal end of each leg of a surgical staple contacting the crown of the adjacent preceding staple, each staple having at least one bend in the crown such that the distal ends of said legs of each staple in an essentially symmetrical converging relationship, and said biasing means acts only on the proximal staple, whereby the plurality of staples are self-aligning on the staple feed track.

2. A cartridge of claim 1 wherein said staple feed track comprises two opposed grooves.

3. A cartridge of claim 1 wherein said crown has two bends.

4. A cartridge of claim 3 wherein said bends are equidistant from the center of said crown.

* * * * *